United States Patent [19]
Nastke et al.

[11] Patent Number: 5,908,632
[45] Date of Patent: Jun. 1, 1999

[54] PROCESS FOR THE PREPARATION OF SPHERICAL MICROPARTICLES CONTAINING BIOLOGICALLY ACTIVE COMPOUNDS

[75] Inventors: Rudolf Nastke, Rehbrücke, Germany; Ernst Neuenschwander, Riehen, Switzerland

[73] Assignee: Novartis Corporation, Summit, N.J.

[21] Appl. No.: 08/776,401

[22] PCT Filed: Jul. 12, 1995

[86] PCT No.: PCT/EP95/02727

§ 371 Date: Jan. 21, 1997

§ 102(e) Date: Jan. 21, 1997

[87] PCT Pub. No.: WO96/03040

PCT Pub. Date: Feb. 8, 1996

[30] Foreign Application Priority Data

Jul. 22, 1994 [CH] Switzerland .............................. 2329/94

[51] Int. Cl.⁶ ..................................................... A01N 25/28
[52] U.S. Cl. .......................... 424/417; 424/419; 424/420; 424/489; 424/490; 424/497; 424/498; 424/501; 424/502; 427/213.3; 427/213.34; 427/213.36; 523/223
[58] Field of Search ..................................... 424/405, 417, 424/419, 420, 489, 490, 497, 498, 501, 502; 427/213.3, 213.34, 213.36; 523/223

[56] References Cited

U.S. PATENT DOCUMENTS 5,576,009  11/1996  Nastke et al. ............................ 424/408

FOREIGN PATENT DOCUMENTS

| 0368576 | 5/1990 | European Pat. Off. . |
| 0379379 | 7/1990 | European Pat. Off. . |
| 2332053 | 6/1977 | France . |
| 1518568 | 7/1978 | United Kingdom . |

OTHER PUBLICATIONS

Derwent Abstract 89–059198.

*Primary Examiner*—Nathan M. Nutter
*Attorney, Agent, or Firm*—William A. Teoli, Jr.; John D. Peabody, III

[57] ABSTRACT

The invention relates to a process for encapsulating biologically active compounds in the form of substantially spherical microparticles, comprising the steps of a) preparing an aqueous solution of surfactants, catalysts and monomers or prepolymers which are suitable for forming a crosslinked polycondensate, b) forming an emulsion of the substantially water-insoluble biologically active compound or mixture thereof in the solution a) by adding said solution under high shear force, and c) forming a solid capsule wall around the biologically active compound or mixture thereof by heating the reaction mixture to a temperature at which the crosslinking reaction tales place, which process comprises fusing the biologically active compound or mixture thereof and adding the melt to the aqueous reaction mixture at a temperature which is higher than the temperature of the reaction mixture.

24 Claims, No Drawings

PROCESS FOR THE PREPARATION OF SPHERICAL MICROPARTICLES CONTAINING BIOLOGICALLY ACTIVE COMPOUNDS

CONTINUING DATA

This application is filed under 35 USC 371 of PCT/EP95/02727, filed Jul. 12, 1995.

The present invention relates to a process for the preparation of spherical microparticles containing biologically active compounds by addition of the preheated compound to the reaction solution. The invention also relates to the use of said microparticles for the preparation of a composition for controlling plant pests, weeds or animal parasites as well as to aqueous spray mixtures containing the microparticles obtained in the practice of this invention.

The microencapsulation of active ingredients in polymeric materials with different polymers is known and can be carried out by various methods, as described for example in Encyclopedia of Polymer Science, John Wiley Sons, 1968, Vol. 8, pp. 719–736.

Particular demands are made of the release properties of biologically active agrochemicals. The applied microparticles must, on the one hand, be comparably active in field application to e.g. emulsifiable concentrates, and, on the the other, as small an amount as possible shall be released on skin contact, so that a high degree of handling safety is ensured. Amino resins are of ten used as polymeric encapsulating materials for microparticles that contain agrochemical compounds. An overview of the broad field of use of these resins for microencapsulation is given, inter alia, in Acta Polymerica 40, (1989) No. 4, pp. 243–251.

The preparation and properties of microparticles prepared with self-crosslinking amino resins are described in Acta Polymerica 40, (1989) No. 5, pp. 325–331. In the processes referred to therein, the starting materials are solid compounds which are e.g. additionally ground to give a fine dispersion in the aqueous polymer solution and are then encapsulated. The drawback of this process is that the solid materials have to be ground to an average particle size of c. 10–30 $\mu$m. Depending on the crystal modification, the time investment and the loss of grinding stock may be considerable. The formation of unwanted and very finely particulate dust constitutes a further problem in this process, especially in lengthy grinding. The grinding process generally results in a broad granular distribution of the grinding stock ranging from very fine dust to fairly large particles. It is also known that the irregular shape of grinding stock particles requires a thick capsule wall for their complete encapsulation, thereby impairing the release properties and often resulting in the formation of unwanted agglomerates.

EP-A-0,379,379 claims a composition and a process for the preparation thereof in which the microparticles are formed by coacervation of at least two water-soluble polymers. The active ingredient is dissolved together with a polymer in an organic solvent, the water-soluble polymers are dissolved in water, and both solutions are combined, with stirring. In a preferred composition, the active ingredient has a melting point below 80° C. and is added in the melt to the aqueous solution at a temperature such that it remains in the molten state. Stable aqueous dispersions of microparticles are obtained. One drawback of this process is that the claimed active ingredients must have low melting points.

EP-A-0,368,576 claims a process for encapsulating chlorpyrifos in a urea-formaldehyde or melamine-formaldehyde resin, wherein in particular the high termite toxicity is also retained in the alkaline range—e.g. when applied to concrete—and the handling safety of these microcapsules is greatly enhanced as compared with e.g. that of an emulsifiable concentrate. Chlorpyrifos (melting point 42–43° C.) is fused and the melt is added to a polymer solution, while the temperature of the reaction medium (polymer solution) may not be below the melting point of chlorpyrifos. The temperature is afterwards raised to 50° C. and the cationic urea-formaldehyde resin is crosslinked under acid conditions. The temperature of the fused chlorpyrifos is always below the temperature of the reaction mixture. In this process too it is only possible to use low-melting active ingredients or melts at low temperature.

It has now been found that it is also possible to stir active ingredients having substantially higher melting points, or melts having substantially higher temperatures, direct into the solution without the high temperature difference resulting in the formation of agglomerates or in larger particle diameters. It is also not necessary for the temperature of the reaction solution to be high when adding the active ingredient, so that this latter remains in the melt state. It has further been found that the microparticles form particularly rapidly, as the first polymer layer surrounding the particles undergoes a change in temperature via the crosslinking temperature and forms a first thin polymer layer. The particles are therefore almost spherical and completely encapsulated by the polymer, even if only a minor amount of polymeric material is deposited. The dried microparticles form a readily free-flowing powder. Additional advantages result from the preparation of the microcapsules. For example, the excess heat resulting from the high temperature of the melt can be utilised to increase the temperature of the aqueous polymer solution to the crosslinking temperature of the wall-forming material. The ensuing melt heat of the active ingredients can further be utilised with particular advantage if the melting point is above the temperature of the aqueous polymer solution.

The active ingredient encapsulated in the microparticles of this invention is released approximately uniformly over an extended period of time from the microparticles, so that a good activity is achieved. The resultant microparticle distribution is very narrow: typically ±5 $\mu$m of the average for 92% of all microparticles is achieved. The process is particularly economic, as grinding can be dispensed with and the heat generated can be utilised for further process steps.

In one of its aspects, therefore, the invention relates to a process for encapsulating biologically active compounds in the form of substantially spherical microparticles, comprising the steps of a) preparing an aqueous solution of surfactants, catalysts and monomers or prepolymers which are suitable for forming a crosslinked polycondensate, b) forming an emulsion of the substantially water-insoluble biologically active compound or mixture thereof in the solution a) by adding said solution under high shear force, and c) forming a solid capsule wall around the biologically active compound or mixture thereof by heating the reaction mixture to a temperature at which the crosslinking reaction takes place, which process comprises fusing the biologically active compound or mixture thereof and adding the melt to the aqueous reaction mixture at a temperature which is higher than the temperature of the reaction mixture.

The spherical microparticles preferably have an average diameter of 0.5 to 500 $\mu$m. More preferably the microparticles have an average diameter of 0.5 to 100 μm and, most preferably, of 0.5 to 20 μm.

The polycondensate is preferably 3 to 40% by weight, and the biologically active compound is 97 to 60% by weight, of the total weight of the microparticles.

The precondensate is preferably an amino resin, most preferably a polycondensate of melamine and formaldehyde, a wholly or partially etherified melamine-formaldehyde condensate, a urea-formaldehyde condensate, a benzoguanamine-formaldehyde condensate, or a urea-glyoxal condensate. Instead of formaldehyde, it is also possible to use other aldehydes singly or in conjunction with formaldehyde.

The molar ratios of urea to formaldehyde are 1:2.5 to 1:3.5, preferably 1:2.7 to 1:3.2.

The molar ratios of melamine to formaldehyde can be 1:3.5 to 1:8, preferably 1:4 to 1:6. The degree of etherification of these resins can be adjusted by the molar ratio of melamine to methanol and is typically c. 1:10 to 1:20, preferably c. 1:15 to 1:18.

Suitable amino resins for forming microparticles will be found, inter alia, in Kirk-Othmer, Encyclopedia of Chemical Technology, 3rd edition, Vol. 2, pp. 440–469.

The polycondensate is most preferably a melamine and formaldehyde polycondensate, a wholly or partially etherified melamine and formaldehyde polycondensate, or a urea-formaldehyde condensate.

The biologically active compound is preferably a pesticide or a mixture of pesticides, and is most preferably a herbicide, an insecticide, an acaricide, a nematicide, an ectoparasiticide, a fungicide or a mixture thereof.

Typical examples of pesticides are: urea derivatives, triazines, triazoles, carbamates, phosphoric acid esters, dinitroanilines, morpholines, acylalanines, pyrethroids, benzilic acid esters and polycyclic halogenated hydrocarbons.

Specific examples of pesticides suitable for use in the practice of this invention are listed hereinbelow (common names as given in The Pesticide Manual, 9th Edition, British Crop Protection Council):

Urea derivatives
  Chlorbromuron, chloroxuron, chlorotoluron, fluometuron, thiazafluron and triasulfuron.
Halogenated acetanilides
  Dimethachlor, alachlor, propachlor.
s-Triazines
  Atrazine, propazine, terbuthylazine, ametryn, aziprotryne, cyromazine.
Triazole derivatives
  Etaconazole, 1-[2-(2,4-dichlorophenyl)-pent- 1 -yl]-1H-1,2,4-triazole, triadimefon, difenoconazole.
Carbamates
  Dioxacarb, aldicarb, benomyl.
Phosphoric acid esters
  Methidathion, anilofos, azinphos methyl, fenamiphos, azamethiphos.
Dinitroanilines
  Benfluralin, pendimethalin, butralin, fluchloralin.
Acylalanines
  Metalaxyl, fluralaxyl, benzoylprop ethyl, flamprop methyl.
Pyrethroids
  Cypermethrin, resmethrin, tetramethrin.
Benzilic acid esters
  Bromopropylates, chlorobenzilates, chloropropylates.
Miscellaneous
  Bromoxynil, ioxynil, oxadiazon, dicofol, fenoxycarb.

Preferred pesticides are S-2,3-dihydro-5-methoxy-2-oxo-1,3,4 thiadiazol-3-ylmethyl O,O-dimethyl phosphorodithioate (=methidathion) and 2-phenylamino-4-methyl-6-cyclopropylpyrimidine.

The temperature of the fused form or of the heated liquid form of the biologically active compound or mixture thereof is above the temperature of the aqueous solution. Preferably it is not less than 60° C. and, most preferably, 100° C., but may not exceed 200° C.

A preferred embodiment of the process is that wherein the difference between the temperature of the melt and the temperature of the aqueous solution is 5 to 100° C.

The temperature range of the aqueous solution of the prepolymer is preferably from 20 to 80° C., most preferably from 30 to 45° C.

The prepolymer is preferably used in a concentration of 5 to 50 g per 100 g of water.

The aqueous solution may contain, in addition to the prepolymer, one or more than one water-soluble oligomer or polymer as emulsifier or dispersant. The surfactants customarily used in formulation technology are described, inter alia, in the following publications:

"McCutcheon's Detergents and Emulsifiers Annual", McPublishing Corp., Glen Rock, N.J., USA, 1988, H. Stache, "Tensid-Taschenbuch" (Handbook of Surfactants), 2nd edition, C. Hanser Verlag Munich, Vienna 1981, M. and J. Ash. "Encyclopedia of Surfactants", Vol. I–III, Chemical Publishing Co., New York, 1980–1981.

The surfactants are preferably nonionic surfactants such as polyethylene glycols, polyethylene glycol monoalkyl ethers, polyethylene glycol-polypropylene glycol copolymers.

Waxes may also be used as adjuvants. These may be natural waxes, modified natural waxes, or semi-synthetic or fully synthetic waxes. It is preferred to use paraffin waxes. Conventional waxes are described, inter alia, in Ullmanns Enzyklopädie der technischen Chemie, 4th edition 1983, Vol. 24, pp. 1–46. The waxes are preferably fused together with the biologically active compound and the melt is then added to the aqueous reaction mixture.

Methods of producing high shear forces are known per se. It is preferred to use a high-speed impeller or a rotary homogeniser.

In another of its aspects, the invention relates to a process for controlling plant pests, weeds or animal parasites, which comprises suspending the novel microparticles in a biologically active concentration in water and applying the suspension so obtained to the pests or to the locus thereof.

In yet another of its aspects, the invention relates to the use of the novel microparticles for the preparation of a composition for controlling plant pests, weeds or animal parasites, and to water-dilutable powders, water-dispersible granules or aqueous spray mixtures containing said microparticles.

The invention is illustrated by the following Examples.

Examples for the preparation of the precondensates.

EXAMPLE A1

Preparation of a urea-formaldehyde precondensate

With stirring, 20 g (0.33 mol) of urea are dissolved in 100 g (1 mol) of a 30% aqueous solution of formaldehyde. The pH is adjusted with 1N aqueous NaOH to 8.5–9.5 and the solution is then heated to a temperature of 70° C. and further stirred slowly for 60 minutes at this temperature. The solution is afterwards cooled to room temperature.

EXAMPLE A2

Preparation of a modified melaimine-formaldehyde precondensate

With stirring, 28 g of melamine (0.22 mol) are added to 124 ml of a 30% aqueous solution of formaldehyde. The reaction mixture is adjusted with 1N aqueous NaOH to pH 9 and heated to 94° C., whereupon the melamine dissolves while reacting with the aldehyde. The reaction mixture is then cooled to 62° C. and, after addition of 120 ml of methanol (3.75 mol) and 7 ml of a 15% aqueous solution of hydrochloric acid, the reaction is carried out at 62° C. for 30 minutes. Then 2.8 g of triethanolamine are added and the azeotropic mixture of methanol-water is distilled from the reaction mixture. After adjustment to a solids content of c. 40 to 60% by weight, 6 g of urea are added to the solution, which is then cooled to room temperature.

Example for the preparation of the microparticles.

EXAMPLE B1

120 ml of water and 24 g of the precondensate prepared according to

Example A2 as well as 3 g of polyethylene glycol (molecular weight 300) are charged to a reactor with temperature control. The reaction mixture is heated to 60° C. and acidified with 12 ml of 2N aqueous citric acid. While stirring with a high-speed impeller of the Ultraturrax type at 12,000 rpm, 50 g of fused 2-phenylamino-4-methyl-6-cyclopropyl-pyrimidine are added and at a temperature of 85° C. After a reaction time of 10 minutes, stirring is continued with a paddle agitator at 500 rpm for 120 minutes at 60° C., giving a suspension of fine particles having an average diameter of c. 7.5 $\mu$m. The particles have a spherical form, are not agglomerated, and have a narrow particle size distribution. The suspension can be further formulated direct in conventional manner or the particles can be dried to give a free-flowing powder.

EXAMPLE B2

The procedure of Example B1 is repeated, using the precondensate of

Example A1. After a reaction time of 5 minutes, acidification is additionally effected with 6 ml of an aqueous 1N solution of HCl to give a suspension of fine particles having an average diameter of c. 7.5 $\mu$m. The particles have a spherical form, are not agglomerated, and have a narrow particle size distribution. The suspension can be further formulated direct in conventional manner or the particles can be dried to give a free-flowing powder.

EXAMPLE B3

60 ml of water and 3 g of the precondensate obtained according to

Example A2 as well as 0.15 ml of polyethylene glycol (molecular weight 300) are charged to a reactor with temperature control. The reaction mixture is heated to 40° C. and then acidified with 2.1 ml of a 2N aqueous solution of citric acid. With stirring (Ultraturrax, 12 000 rpm), 12.6 g of fused methidathion heated to 60° C. are added to the reaction mixture and the mixture is stirred for 10 minutes at this speed. Stirring is then continued at 60° C. with a propeller stirrer at 500 rpm for 120 minutes. The batch is then cooled to give a suspension of fine spherical particles having diameters of 1 to 10 $\mu$m.

EXAMPLE B4

The procedure described in Example B3 is repeated. A paraffin wax which melts at 100–120° C. is fused together with the methidathion and the melt is further heated to 150° C. The melt heated to this temperature is added direct to the reaction solution and the procedure described in Example B3 is carried out to give a suspension of fine spherical particles having diameters of 1 to 10 $\mu$m.

What is claimed is:

1. A process for encapsulating a biologically active compound in the form of substantially spherical microparticles, comprising the steps of
   a) preparing an aqueous solution of surfactants, catalysts and monomers or prepolymers which are suitable for forming a crosslinked polycondensate,
   b) forming an emulsion of the substantially water-insoluble biologically active compound or mixture thereof in the solution a) by adding said solution under high shear force, and
   c) forming a solid capsule wall around the biologically active compound or mixture thereof by heating the reaction mixture to a temperature at which the crosslinking reaction takes place,
   which process comprises fusing the biologically active compound or mixture thereof and adding the melt to the aqueous reaction mixture at a temperature which is higher than the temperature of the reaction mixture.

2. A process according to claim 1, wherein the spherical microparticles have an average diameter of 0.5 to 500 $\mu$m.

3. A process according to claim 1, wherein the spherical microparticles have an average diameter of 0.5 to 100 $\mu$m.

4. A process according to claim 1, wherein the spherical microparticles have an average diameter of 0.5 to 20 $\mu$m.

5. A process according to claim 1, wherein the polycondensate is 3 to 40% by weight, and the biologically active compound is 97 to 60% by weight, of the total weight of the microparticles.

6. A process according to claim 1, wherein the precondensate is an amino resin.

7. A process according to claim 1, wherein the polycondensate is a melamine-formaldehyde condensate, a wholly or partially etherified urea-formaldehyde condensate, a benzoguanamine-formaldehyde condensate or a urea-glyoxal condensate.

8. A process according to claim 7, wherein the polycondensate is a melamine-formaldehyde condensate, a wholly or partially etherified melamine-formaldehyde condensate, or a urea-formaldehyde condensate.

9. A process according to claim 1, wherein the biologically active compound is a pesticide or a mixture of pesticides.

10. A process according to claim 9, wherein the biologically active compound is a herbicide, an insecticide, an acaricide, a nematicide, an ectoparasiticide, a fungicide or a mixture thereof.

11. A process according to claim 1, wherein the biologically active compound is S-2,3-dihydro-5-methoxy-2-oxo-1,3,4 thiadiazol-3-ylmethyl O,O-dimethyl phosphorodithioate (=methidathion) or 2-phenylamino-4-methyl-6-cyclopropylpyrimidine.

12. A process according to claim 1, wherein the temperature of the melt of the biologically active compound or mixture thereof is above the temperature of the aqueous solution.

13. A process according to claim 1, wherein the temperature of the melt of the biologically active compound or mixture thereof is not less than 60° C.

14. A process according to claim 1, wherein the temperature of the melt of the biologically active compound or mixture thereof is not less than 100° C. and not higher than 200° C.

15. A process according to claim 1, wherein the temperature of the aqueous solution containing the prepolymer is in the range from 40 to 80° C.

16. A process according to claim 1, wherein the temperature of the aqueous solution containing the prepolymer is in the range from 30 to 45° C.

17. A process according to claim 1, wherein the difference between the temperature of the melt and the temperature of the aqueous solution is from 5 to 100° C.

18. A process according to claim 1, wherein the prepolymer is used in a concentration of 5 to 50 g per 100 g of water.

19. A process according to claim 1, which comprises fusing a natural wax, a modified natural wax, a semi-synthetic or fully synthetic wax together with the biologically active compound or mixture thereof and then adding this melt to the aqueous reaction mixture.

20. A process according to claim 19, wherein the wax is a paraffin wax.

21. A process according to claim 19, wherein the high shearing force is produced by a high-speed impeller.

22. A process according to claim 19, wherein the high shearing force is produced by a rotary homogeniser.

23. An aqueous suspension comprising a pesticidally effective amount of the microparticle product produced by the process of claim 1.

24. A method of controlling plant pests, weeds or animal parasites comprising the step of applying the suspension of claim 23 to the plant pests, weeds or animal parasites, or the locus thereof.

* * * * *